United States Patent [19]

Joh et al.

[11] Patent Number: 4,604,412

[45] Date of Patent: Aug. 5, 1986

[54] STABLE POLYMER EMULSION COMPOSITION CAPABLE OF GIVING A THROMBORESISTANT SURFACE, AND PROCESS FOR PRODUCTION THEREOF

[75] Inventors: Yasushi Joh, Yokohama; Toshio Nagase, Houjyoshin; Noriaki Kaneko, Kawasaki, all of Japan

[73] Assignee: Nippon Zeon Co., LTD., Tokyo, Japan

[21] Appl. No.: 475,499

[22] Filed: Mar. 15, 1983

[30] Foreign Application Priority Data

Mar. 17, 1982 [JP] Japan ................................. 57-41865

[51] Int. Cl.$^4$ ...................... C08L 83/06; C09D 5/00; C09K 3/00
[52] U.S. Cl. .................................. 523/112; 524/108; 524/111; 524/500; 524/539; 525/440; 525/452; 525/460; 525/903
[58] Field of Search ................ 523/112; 524/108, 111, 524/265, 500, 539; 525/452, 459, 460, 440

[56] References Cited

U.S. PATENT DOCUMENTS

| | | | |
|---|---|---|---|
| 3,562,352 | 2/1971 | Nyilas | 525/460 |
| 3,746,683 | 7/1973 | Salyer | 525/460 |
| 3,941,733 | 3/1976 | Chang | 525/460 |
| 4,202,807 | 5/1980 | Moretto | 524/265 |

*Primary Examiner*—C. Warren Ivy
*Attorney, Agent, or Firm*—Sherman and Shalloway

[57] ABSTRACT

A stable polymer emulsion composition capable of giving a thromboresistant surface, said composition comprising polyurethane, a polydiorganosiloxane, and a cyclic ether, said polydiorganosiloxane being dispersed as particles having an average particle diameter of 0.1 to 50 microns in a solution of the polyurethane in the cyclic ether, and at least a part of the surfaces of said particles being crosslinked. The said composition can be prepared by dispersing a polydiorganosiloxane having a hydroxyl or acetate end group as fine particles in a solution of polyurethane in a cyclic ether to form an emulsion, and reacting the polydiorganosiloxane with a crosslinking agent to crosslink at least a part of the surfaces of the particles in the presence of 10 to 500 ppm of water.

33 Claims, No Drawings

STABLE POLYMER EMULSION COMPOSITION CAPABLE OF GIVING A THROMBORESISTANT SURFACE, AND PROCESS FOR PRODUCTION THEREOF

This invention relates to a polymer composition having anti-thrombogenic properties. More specifically, this invention relates to a coating polymer composition capable of forming an excellent thromboresistant surface, and a process for production thereof.

In recent years, blood-contact medical devices have shown a rapid improvement with the development of antithrombogenic materials. Antithrombogenic properties must be imparted to medical devices which come into contact with blood in their therapeutic use. Examples of these devices are artificial kidneys, intravascular dwelling catheters, blood bags, and artificial hearts. Artificial hearts require especially good antithrombogenicity and blood compatibility. No medical devices have yet been developed which completely meet this requirement.

Polydialkylsiloxane-polyurethane block copolymers have been known as antithrombogenic materials. U.S. Pat. No. 3,562,352 proposes a block copolymer as a hemocompatible material in which blocks of polyurethane are bonded to blocks of a polydialkylsiloxane with silicon-nitrogen bonds. Japanese Patent Publication No. 8177/1980 discloses that a surface coated with a polydimethylsiloxane-polyurethane block copolymer develops antithrombogenic properties when it is of a heterogeneous micro domain structure of 0.1 to 3 microns. In order to form such a heterogeneous micro domain structure, the polymeric substance is preferably a block copolymer; and that the aforesaid block copolymer shows better antithrombogenicity than either polydimethylsiloxane or polyurethane alone.

In order to develop better antithrombogenic materials, the present inventors carefully investigated the antithrombogenicity of the polyurethane-polydimethylsiloxane system. In the course of this investigation, they found that a solution of the aforesaid two polymers in a cyclic ether solvent shows a homogeneous emulsion composition in which one of the components is phase-separated and dispersed microscopically when the total concentration of the polymers exceeds a certain value. A surface coated with this emulsion composition surprisingly shows better antithrombogenicity than a surface coated with a uniform solution of the composition with a low total concentration of the aforesaid two polymers.

It is an object of this invention therefore to provide an antithrombogenic polymer composition capable of giving a blood-contact surface having excellent antithrombogenic properties and a process for its preparation. A medical device having excellent antithrombogenic properties can be produced by coating this polymer composition on the blood contact surface of the medical device.

The composition of this invention is characterized by the fact that it is not a complete solution of the polydiorganosiloxane and polyurethane in the ether solvent, but is an emulsion composition in which the micro-phase separated polydiorganosiloxane is dispersed in the solution as particles having an average particle diameter of 0.1 to 50 microns. The emulsion is quite stable because at least a part of the surface of the polydiorganosiloxane particles is crosslinked to form a stable spherical surface and the crosslinked networks have interpenetrating polyurethane chain entanglements.

The polymeric substances to form the emulsion composition of this invention are polyurethane and a polydiorganosiloxane. When polyurethane or the polydiorganosiloxane is independently dissolved in a cyclic ether such as tetrahydrofuran, or dioxane, or a mixture of these, a uniform clear solution is formed. But when the polyurethane and polydiorganosiloxane are dissolved together in the above solvent, micro-phase separation usually occurs, and the resulting liquid becomes milk-white. This micro-phase separation appears when the total amount of the two polymeric substances increases to a certain value, usually when the total concentration exceeds 3.5%. When the total concentration exceeds 4%, a turbid milk-white emulsion is usually obtained. This turbidity is attributed to the formation of the fine particles which disperse in a viscous medium (the sea component ie continuous phase) in the solution. Which of these polymers becomes the sea component or the island component (separated fine particles) depends upon the ratio between the two polymers. Usually, the major component forms the sea, and the minor component disperses as an island (ie forms disperse phase).

Various compositions were prepared by using a polydiorganosiloxane, polyurethane and a cyclic ether, and their antithrombogenic properties were examined. It was found that excellent antithrombogenic properties can be obtained with a surface coated with a homogeneous milk-white emulsion composition which was prepared by increasing the total amount of the two polymers to form micro-separated fine particles of the polydiorganosiloxane which were stabilized by reaction with a crosslinking agent in the presence of water. The antithrombogenicity of a surface coated with this reacted emulsion was found to be far better than a surface coated with a clear solution prepared by dissolving the two polymers uniformly in the cyclic ether at low total concentrations of the two polymers. It has also been found that a coated film obtained from this emulsion composition was tough.

The most important feature of the present invention is that the size of the fine particles of the polydiorganosiloxane as an island component play an important role in developing antithrombogenicity or hemocompatibility. When the average particle size of these fine particles exceeds 50 microns, the coated surface does not show satisfactory antithrombogenicity. The particle size should be not more than 50 microns, preferably not more than 10 microns, more preferably not more than 5 microns to obtain good antithrombogenicity.

It should be noted that in order to obtain the above desirable hemocompatibility or antithrombogenicity, it is necessary that the fine particles of polydiorganosiloxane in the emulsion should be subjected to crosslinking reaction in the presence of water. A mere blend of the same components without crosslinking reaction does not show satisfactory antithrombogenicity.

The emulsion composition in which the polydiorganosiloxane particles having the aforesaid particle size are dispersed cannot thermodynamically maintain a stable emulsion condition unless some measure is taken, for example unless it is continuously agitated. When the mere blend of the polyurethane and polydiorganosiloxane in a cyclic ether is used, a similar kind of apparent emulsion can be obtained by continuous agitation, but this apparent emulsion is easily destroyed, upon stopping the stirring. Specifically, the fine dispersed particles coalesce and merge to become larger with time, and finally the emulsion is destroyed completely into two layers (a polyurethane solution layer (lower phase) and a polydiorganosiloxane solution layer (upper phase)).

The key to the successful preparation of a stable emulsion composition in which the particle size of the polydiorganosiloxane is maintained in the range of 0.1 to 50 microns lies in the fact that at least a part of a surface of the polydiorganosiloxane particles is cross-linked to form a stable spherical surface. It is important in this invention that the above-mentioned crosslinking reaction should proceed in the finely dispersed emulsion in the presence of water.

The polydiorganosiloxane used in this invention is a silicone polymer composed of units of the general formula

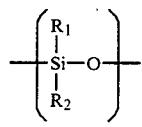

wherein $R_1$ and $R_2$ each represent an alkyl group, an aryl group, an alkenyl group, or a halogenated hydrocarbon group.

Polydimethylsiloxane is most preferably used. Other examples include polydiethylsiloxane, polymethylphenylsiloxane, dimethylsiloxane/diphenylsiloxane copolymer, and polymethylphenylvinylsiloxane.

Polydiorganosiloxanes used in this invention must have active end groups (e.g., a hydroxyl group, an acetate group) which undergo crosslinking reaction with the so-called RTV (room temperature vulcanizing) crosslinking agent described hereinbelow. Polydimethylsiloxane having terminal —OH groups or terminal acetate groups is most useful. Preferably, the polydimethylsiloxane has a molecular weight in the range of from 5,000 to 200,000, more preferably from 10,000 to 80,000.

The polyurethane used in this invention is not restricted except that it should be soluble in cyclic ethers. Both polyester polyurethanes and polyether polyurethanes, which are produced by known methods described, for example, in U.S. Pat. No. 3,562,352, can be used.

Examples of the polyester polyurethanes are those obtained by reaction between hydroxyl-terminated polyesters and diisocyanates such as ethylene diisocyanate, 2,4-tolylene diisocyanate and diphenylmethane diisocyanate to form an isocyanate terminated prepolymer, followed by chain extending reaction to form high molecular weight polyurethanes. The hydroxyl-terminated polyester can be prepared by reaction between a glycol such as ethylene glycol or diethylene glycol or a polyhydric alcohol such as trimethylolpropane or glycerol and a polycarboxylic acid such as adipic acid or succinic acid.

Examples of the polyether polyurethanes are those obtained by reaction between hydroxyl-terminated polyethers and the aforesaid diisocyanates to form prepolymers having isocyanate terminal groups, which are combined by chain extenders to form high molecular weight polyether polyurethanes. The polyethers having hydroxyl end groups are polymers of an alkylene oxide such as ethylene oxide and 1,2-propylene oxide or copolymers of an alkylene oxide and a polyhydric alcohol such as propylene glycol or 1,2,6-hexanetriol or a polymer from tetrahydrofuran.

Diamines, hydrazines, or glycols such as ethylene glycol, tetramethylene glycol may be used as chain extenders in the production of polyurethane in this invention.

Polyester or polyether polyurethanes obtained by reacting isocyanate-terminated prepolymers with hydroxyl-terminated chain extenders are especially suitable as the polyurethane used in this invention.

In the practical use of this invention, the ratio between the polyurethane and the polydiorganosiloxane can be varied over a wide range. The amount of the polydiorganosiloxane in the mixture is usually 0.1 to 50% by weight, preferably 0.2 to 50% by weight, more preferably 0.5 to 30% by weight, especially preferably 1 to 20% by weight.

When the amount of the polydiorganosiloxane is smaller than the lower limit given above, the resulting emulsion composition does not give a good result, that is, it gives a coated film having poor elastic properties and strength. When the proportion of the polydiorganosiloxane used exceeds 50% by weight, it is quite difficult to adjust the particle size of the dispersed polydiorganosiloxane to the above-specified range. Furthermore, if the proportion of the polydiorganosiloxane is less than 0.1% by weight, antithrombogenic properties cannot be obtained as expected.

In order to crosslink at least a part of the surface of the polydiorganosiloxane particles in accordance with this invention, it is necessary to use the specified crosslinking agents. The desirable crosslinking agents are so-called RTV's which function as effective crosslinking agents in the presence of water at room temperature. They have active groups such as $\equiv$SiOH, $\equiv$Si—CH=CH$_2$, $\equiv$SiH, $\equiv$SiOR (R=CH$_3$, C$_2$H$_5$, etc.), and $\equiv$SiOCOR (R=CH$_3$, C$_2$H$_5$, etc.). Examples of these compounds are those of the general formula R$_n$Si(OR')$_{4-n}$ wherein R represents an alkyl group, an aryl group, etc., R' represents an alkyl group, an acyl group, etc., and n is 0 or 1. Typical examples are methyltriacetoxysilane, ethyltriacetoxysilane, methyltrimethoxysilane, phenylytriacetoxysilane, methyltrimethoxysilane, ethyltriethoxysilane, phenyltriethoxysilane and trimethyltrifluoroacetoxysilane; and silane compounds including vinyltriacetoxysilane, vinyltrimethoxysilane, aminosilane, aminoxysilane and amidosilane. These examples are not limitative.

The amount of the crosslinking agent used is preferably 2 to 20% by weight, more preferably 4 to 15% by weight, especially preferably 6 to 10% by weight, based on the polydiorganosiloxane. When the amount of the crosslinking agent is less than 2% by weight based on polydiorganosiloxane, the emulsion composition obtained becomes unstable, and the effect contemplated by this invention cannot be obtained. On the other hand, when the amount of the above crosslinking agent is larger than 20% by weight based on polydiorganosiloxane used, crosslinking reaction proceeds excessively to cause gellation. Therefore, this should be avoided.

In the practical application of this invention, the solvents used in the formation of the emulsion are required to be easily removed by evaporation or washing with water from the coated film. Therefore, solvents having a low boiling point, for examples, less than 110° C. are preferred. Desirably, they are water-soluble cyclic ethers because they are easy to remove by washing with water. The solvents which fulfill these requirements are cyclic ethers such as tetrahydrofuran and dioxane. Anisole is not favorable because of its high boiling point, and ethyl ether or butyl ether is not suitable because of its insolubility in water. In the present invention, the cyclic ether solvents may be used singly or as a mixture. In order to obtain excellent antithrombogenic properties, it is preferred to use a mixture of tetrahydrofuran and dioxane. The preferred weight ratio of dioxane to tetrahydrofuran is not more than 1, more preferably from 1:1 to 1:4, especially preferably from 1:1.5 to 1:3.0. When the ratio is higher than 1, the stability of the emulsion becomes poor. When the ratio is less than 1:4, the antithrombogenicity of the emulsion composition is reduced.

Another solvent such as an alcohol may be included in the ether solvent in an amount which does not greatly affect the practice of the present invention.

In order to prepare the stable polymer emulsion composition of this invention, the polydiorganosiloxane and polyurethane in the aforesaid mixing proportions are mixed with the cyclic ether so that the total concentration of these polymers is preferably at least 4% by weight, more preferably 8 to 20% by weight, based on the resulting emulsion composition; and the mixture must be reacted under special conditions. To disperse the micro-phase separated polydiorganosiloxane to a size of 50μ or below, the mixture must be stirred. When the stirring is carried out by using a stirrer having an ordinary shearing force, the particle size of the dispersed particles of the polydiorganosiloxane can be adjusted to 50 microns or below. When a particle size of 20 microns or below is desired in order to obtain a better thromboresistant surface, the use of a stirrer having a high shearing force, such as a homogenizer, is desirable. There is no particular restriction on the temperature used during the reaction. In order to promote dissolution of the polymers, temperatures of about 40° C. may be adopted.

The simple blend of the above components is very unstable and the size of the dispersed particles of the polydiorganosiloxane becomes larger with time by merging of the particles. Upon standing, the emulsion is destroyed to form a two-phase separated clear solution in which the upper layer is polydiorganosiloxane and the lower layer is polyurethane.

To stabilize the resulting emulsion composition at the desired dispersed particle size, and prevent the size from increasing with the lapse of time, it is necessary to crosslink at least a part of the surface of the dispersed particles of the polydiorganosiloxane. This can be achieved by adding a required amount of the aforesaid crosslinking agent to the emulsion composition. It is very important that the above reaction should proceed in the presence of water. In an anhydrous condition, the same mixture would produce a block copolymer of polydiorganosiloxane and polyurethane with a silicon-nitrogen bond as disclosed in U.S. Pat. No. 3,562,352. However, the inventors found that in the presence of water, quite a different reaction takes place. In the presence of water crosslinking reaction occurs from the particle surface of the dispersed polydiorganosiloxane and the crosslinked networks entangle the polyurethane molecular chains to form interpenetrating polymer networks which stabilize the particles in the emulsion. The formation of the interpenetrating polymer networks between polydiorganosiloxane and polyurethane at the surface of the dispersed particles has closely to do with the excellent homocompatibility and outstanding antithrombogenicity achieved by this invention. The amount of water in this invention should be 10 to 500 ppm, preferably 50 to 300 ppm, more preferably 100 to 200 ppm, especially preferably 80 to 200 ppm.

The reaction temperature for the crosslinking is usually 10° to 100° C., preferably 30° to 50° C. Temperatures lower than the boiling point of the solvent are suitably used.

The reaction time is usually at least 1 hour to two weeks, preferably from 4 hours to 10 days.

When the preparation of the emulsion is carried out under the aforesaid conditions, surprisingly, a very stable emulsion is formed. Again, surprisingly, this remains stable over a long period of time with no appreciable change in its properties, contrary to the current knowledge in this field.

No clear explanation for the formation of such a stable emulsion under the aforesaid conditions has been made. However, the present inventors have found that the surface of dispersed fine particles formed by the micro-phase separation is crosslinked in a network structure over a suitable extent to thereby stabilize the surface of the particles, and that the hydroxyl groups formed by the hydrolysis of the cross-linking agents on the crosslinked networks act like a surface-active agent thereby to stabilize the surface of the particles and increase the affinity of the dispersed particles for the sea component in the emulsion medium. Furthermore, as already described, the cross-linked surface is entangled with polyurethane molecular chains to form interpenetrating polymer networks with polydiorganosiloxane chains, which increases affinity for the sea component on the surface of the dispersed fine particles of the polydiorganosiloxane.

A film or coating formed from the stable polymer emulsion composition of this invention has very good antithrombogenic properties, and excellent blood compatibility. Accordingly, the coated surface formed from the emulsion composition is very useful as a device having a blood-contact surface, for example an intravascular dwelling catheter, a cannula, an extra-corporeal blood circulating circuit, a blood bag, a ventricular assistant device, an artificial heart, etc. Since this coating has excellent mechanical and elastic properties, it is especially suitable for forming a blood-contact portion which pulsates incessantly, such as artificial hearts or intraaortic balloon pumps.

The following examples illustrate the present invention specifically. It should be understood that these examples are merely for illustrative purposes and do not in any way limit the scope of the present invention.

REFERENTIAL EXAMPLE 1

A prepolymer having terminal isocyanate groups was prepared by a known method from polypropylene glycol having an average molecular weight of 1,200 and methylenebis(4-phenylisocyanate). Then, a polyether polyurethane was prepared from the prepolymer by using tetramethyleneglycol as a chain extender. The resulting polyurethane (91 parts by weight) and 9 parts of polydimethylsiloxane (molecular weight 45,000) having terminal hydroxyl groups were dissolved at 40° C. with stirring in a mixed solvent of dioxane and tetrahydrofuran (weight ratio 1:2) which had been dehydrated to a water content of less than 8 ppm. Thus, a viscous solution (polymer concentration 13% by weight) was prepared (solution 1). The solution 1 had a final water content of 9.5 ppm. The solution 1 was divided into two portions. To one portion was added 6.8% by weight, based on the polydimethylsiloxane, of methyltriacetoxysilane, and the mixture was reacted at 40° C. for 12 hours with stirring to form a solution (solution 2).

The solutions 1 and 2, immediately after preparation, were non-transparent viscous liquids. Observation under an optical microscope showed that these liquids were emulsions in which particles (composed mainly of polydimethylsiloxane) having an average particle size of 6 microns were dispersed.

When the stirring was stopped and the solutions 1 and 2 were allowed to stand at room temperatures, the particles rapidly grew with the lapse of time. One day later, the average particle size increased to 50 microns, and the particles showed a tendency to grow further. As a whole, the solutions had a tendency to become less opaque with time.

Two days layer, the solution 1 separated into two layers, and the upper layer was a transparent polydimethylsiloxane solution layer. The solution 2 was a little stabler than the solution 1. But three days later, the emulsion was completely destroyed, and the solution 2 also separated into two layers. The separated polyurethane solution layer (lower layer) and polydimethylsiloxane solution layer (upper layer) were both transparent.

EXAMPLE 1

In this example, the polymer composition was the same as in Referential Example 1, but the water content of the reaction system was adjusted. Specifically, the water content of the polymer mixture was adjusted to 160 ppm. To the resulting solution was added 6.8% by weight of methyltriacetoxysilane which was distilled immediately before use, and the mixture was stirred at 40° C. The reaction was continued at 40° C. for 62 hours with stirring.

The resulting reaction product was similar in appearance to the solution 1 immediately after reaction in Referential Example 1, and the polydimethylsiloxane particles showed a uniform particle size shown by an average particle size of 6 microns. Interestingly, this emulsion was unexpectedly very stable, and remained stable for 6 months without stirring, and that the size of the dispersed polydimethylsiloxane particles was nearly uniform and was 6 microns on an average for a long time.

To define the stability of the emulsion, the solution was placed in a capillary and centrifuged under 10,000G for 30 minutes. The emulsion of this example was stable, as evidenced by the fact that the particles remained almost unchanged. On the other hand, the emulsion in Referential Example 1 showed that a centrifuged force of only 1,000G for 10 minutes is enough to increase the particle sizes, and after 20 minutes, the emulsion was destroyed to form transparent two layers.

EXAMPLE 2

An isocyanate-terminated prepolymer was prepared from polyethylene glycol (average molecular weight 500) and tolylene diisocyanate, and then subjected to chain extension using ethylene glycol as a chain extender to prepare polyurethane. The polyurethane (74 parts by weight) and 26 parts by weight of polydimethylsiloxane (molecular weight 36,000) having terminal acetate groups were dissolved at room temperature with stirring in a fully dehydrated mixed solvent of dioxane and tetrahydrofuran (weight ratio 1:3) to prepare a viscous solution having a polymer concentration 9.0% by weight. Water was added so that the water content of the solution became 120 ppm. Twenty parts by weight of dimethyldiacetoxysilane was added to the resulting solution, and the mixture was stirred at 36° C. for 80 hours.

The resulting composition was a slightly non-transparent emulsion in which particles composed mainly of polydimethylsiloxane and solvent having an average particle diameter of 3.5 microns were dispersed. The emulsion was very stable and did not change for 6 months. A centrifugal test for this emulsion (10,000G, 30 minutes) showed that the emulsion remained unchanged and no tendency to the particle size increase was observed.

REFERENTIAL EXAMPLE 2

One part by weight of polydimethylsiloxane having a molecular weight of 60,000 and 9 parts by weight of polyether polyurethane having a molecular weight of 86,000 were added with stirring to a mixture of tetrahydrofuran and dioxane (weight ratio 2:1). Until the polymer concentration reached 3% by weight, the mixture was slightly opaque but was nearly uniform. The mixture had a water content of 620 ppm. When the polymer concentration exceeded 4% by weight, polydimethylsiloxane was separated and dispersed as fine particles. Under stirring, these particles had an average particle diameter of 5.6 microns. This system was unstable, and when the stirring was stopped, the dispersed polydimethylsiloxane particles associated and became larger, and the size of the dispersed particles became non-uniform. On standing further for 1 week, the polydimethylsiloxane solution layer gathered in the upper portion of the system, and three days later, the system separated into two phases which include non-uniform gelatinous materials.

EXAMPLE 3

One part by weight of polydimethylsiloxane having a molecular weight of 60,000 and containing hydroxyl groups at both ends and 9 parts of the same polyether polyurethane as used in Referential Example 2 were dissolved in 83 parts by weight of a mixed solvent of tetrahydrofuran and dioxane (weight ratio 2:1). Before the dissolution, the water content of the solvent was adjusted to 120 ppm. The concentration of the polymer was about 12% by weight. In the mixture the polydimethylsiloxane was dispersed as fine particles having an average diameter of 4.5 microns. To this, a solution of 0.1 part by weight of methyltriacetoxysilane in 17 parts by weight of a 2:1 mixture of tetrahydrofuran and dioxane was added dropwise with stirring at 35° C. over the course of about one hour to initiate the reaction. After the addition, the mixture was continuously stirred at 35° C. for 24 hours. After 24 hours, the water content of the solution was found to decrease to 60 ppm. This shows that the methyltriacetoxysilane reacted as a crosslinking agent.

The resulting polymer emulsion composition was found to be very stable and had an average dispersed particle diameter of 4.5 microns. On standing for as long as 5 months, this composition did not change at all but remained stable. Even when a centrifugal force of 10,000G was applied, the emulsion was not destroyed, nor the particles associated.

REFERENTIAL EXAMPLE 3

Example 3 was repeated except that the water content of the system was adjusted to 8 ppm.

The resulting system had poor stability, and upon standing for one month, the system was seen to become non-uniform or heterogeneous and undesirable gelation was observed. After 1.5 months, the system separated into two layers. The upper layer was composed mainly of polydimethylsiloxane.

REFERENTIAL EXAMPLE 4

Example 3 was repeated except that the water content of the system was adjusted to 6,000 ppm.

With the lapse of time, the resulting polymer emulsion composition began to form a fine gel-like substaance, and after the lapse of one month, the gel-like substance floated in the upper portion of the system.

EXAMPLE 4

Thirteen parts by weight of commercial thermoplastic polyurethane (ESTANE 5714, a trademark for a product of B. F. Goodrich Chemical Company) was dissolved in a 1:1 mixture of tetrahydrofuran and dioxane to form a solution having a polymer concentration of 10% by weight, and its water content was adjusted to 200 ppm.

Separately, 3 parts by weight of acetate-terminated polydimethylsiloxane having a molecular weight of about 65,000 was dissolved in the same mixed solvent (having a water content of 60 ppm) so that the polymer concentration reached 10% by weight, and 0.2 part by weight of methyltriacetoxysilane was added to form a uniform solution.

While the polyurethane solution was stirred, the above solution containing methyltriacetoxysilane and polydimethylsiloxane was added dropwise at 30° C. over 2 hours, and the mixture was further reacted at 38° C. for 48 hours with stirring.

The resulting emulsion was very stable and the emulsion particles had an average particle diameter of 2.4 microns. It remained stable even after the lapse of 6 months and did not change at all.

In contrast, when the system was dehydrated to a water content of less than 10 ppm, the emulsion obtained was unstable, and separated into two layers upon standing for 2 months. Furthermore, since with the lapse of time, the particles of the emulsion associated non-uniformly and increased in size, Thus, the particle size of the emulsion particles became non-uniform (20 microns to 80 microns).

When the water content was adjusted to more than 500 ppm at the start of the reaction, a gel-like substance formed upon standing for a long period of time (more than 2 weeks).

EXAMPLE 5

A sac-type artificial heart was made by using plasticized polyvinyl chloride containing 80% by weight of dioctyl phthalate based on the polyvinyl chloride. The inside surface of the artificial heart was coated with the polymer emulsion composition obtained in Example 1, 2 or 3. The resulting artificial heart was subjected to a test of a left ventricular bypass pump using a goat. Even after 2 weeks, no thrombus was seen in the inside of the pump.

On the other hand, when the inside surface of the artificial heart was coated with the non-uniform composition obtained in Referential Example 1, 2 or 3 and the artificial heart was subjected to the same test, thrombus was seen to form partly in the inside surface of the artifical heart. Outstanding antithrombogenicity was evidenced by the Lee-White test. Specifically, the emulsions in Examples 1, 2 and 3 showed a blood coagulation time of over 75 minutes, while the solutions in Referential Examples 1, 2 and 3 showed a blood coagulation time of lesss than 30 minutes in the Lee-White test.

What is claimed is:

1. A polymer emulsion composition which is stable against phase separation for extended periods and is capable of forming thromboresistant films, coatings, and surfaces, said composition comprising an emulsion of particles having an average particle diameter of from 0.1 to 50 microns of a polydiorganosiloxane having a weight average molecular weight in the range of from about 5000 to 200,000 and a hydroxyl, vinyl or acetate end group and repeating units of the formula

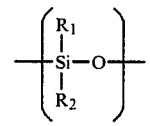

wherein $R_1$ and $R_2$ each independently represent an alkyl group, an aryl group, an alkenyl group or a halogenated hydrocarbon group, in a continuous phase of a solution of a polyether polyurethane or a polyester polyurethane in a cyclic either, wherein the surfaces of the polydiorganosiloxane particles are at last partially crosslinked in the presence of water, and wherein the total amount of the polyurethane and the polydiorganosiloxane is at least 4% by weight based on the weight of the composition and the amount of the polydiorganosiloxane is 0.1 to 50% by weight based on the combined weight of the polydiorganosiloxane and the polyether or polyester polyurethane.

2. The emulsion composition of claim 1 wherein the amount of the polydiorganosiloxane is from 0.2 to 50% by weight based on the combined weight of the polyorganosiloxane and the polyether- or polyester polyurethane.

3. The emulsion composition of claim 1 wherein the amount of the polydiorganosiloxane is from 0.5 to 30% by weight based on the combined weight of the polydiorganosiloxane and the polyether- or polyester polyurethane.

4. The emulsion composition of claim 1 wherein the amount of the polydiorganosiloxane is from 1 to 20% by weight based on the combined weight of the polydiorganosiloxane and the polyether- or polyester polyurethane.

5. The emulsion composition of claim 1 wherein the polyurethane is obtained by chain-extending a prepolymer having isocyanate groups at the ends of the molecular chain with a hydroxyl group-containing compound.

6. The emulsion composition of claim 1 wherein the polydiorganosiloxane has at the ends of the molecular chain an active group selected from a hydroxyl group, an acetate group and a vinyl group.

7. The emulsion composition of claim 1 wherein the cyclic ether is selected from tetrahydrofuran and dioxane.

8. The emulsion composition of claim 18 wherein the polydiorganosiloxane particles are crosslinked with an active group containing silane compound which can effectively crosslink the polydiorganosiloxane particles in the presence of water at room temperature.

9. The emulsion composition of claim 8 wherein the crosslinking agent is a compound of the formula $$R_nSi(OR')_{4-n}$$

wherein R represents an alkyl group or an aryl group, R' represents an alkyl group or an acyl group, and n is 0 to 1.

10. The emulsion composition of claim 8 wherein the crosslinking agent is selected from the group consisting of methyltriacetoxysilane, ethyltriacetoxysilane, methyltrimethoxysilane, phenyltriacetoxysilane, methyltrimethoxysilane, ethyltriethoxysilane, phenyltriethoxysilane, trimethyltrifluoroacetoxysilane, vinyltrimethoxysilane, aminosilane, aminoxysilane and amidosilane.

11. The emulsion composition of claim 1 wherein the cyclic ether is a mixture of tetrahydrofuran and dioxane at a weight ratio of dioxane to tetrahydrofuran of from 1:1 to 1:4.

12. The emulsion composition of claim 1 wherein the cyclic ether is a mixture of tetrahydrofuran and dioxane at a weight ratio of dioxane to tetrahydrofuran of from 1:1.5 to 1:3.0.

13. The emulsion composition of claim 1 wherein the total amount of the polyurethane and the polydiorganosiloxane is from 8 to 20% by weight, based on the total composition.

14. The emulsion composition of claim 1 wherein the polydiorganosiloxane particles have an average particle diameter of from 0.1 to 20 microns.

15. The emulsion composition of claim 1 wherein the polydiorganosiloxane is polydimethylsiloxane.

16. A film formed from the emulsion composition of claim 1.

17. A coating formed from the emulsion composition of claim 1.

18. The emulsion composition of claim 1, wherein the polydiorganosiloxane is crosslinked in the presence of 80 to 500 ppm of water.

19. A process for preparing a polymer emulsion composition which is stable against phase separation over extended periods and is capable of giving a thromboresistant film, coating or surface, which comprises dispersing, under stirring a polydiorganosiloxane having a weight average molecular weight in the range of from about 5,000 to 200,000 and a hydroxyl, vinyl or acetate end group as fine particles in a solution of polyurethane selected from polyether polyurethane and polyester polyurethane in a cyclic ether to form an emulsion, and reacting the polydiorganosiloxane with a cross linking agent which is an active-group containing silane compound to cross link at least a part of the surfaces of the particles in the presence of 80 to 500 ppm of water, the polydiorganosiloxane being present in the mixture in an amount of 0.1 to 50% by weight and the total concentration of polymers being at least 4% by weight based on the resulting emulsion composition.

20. The process of claim 19 wherein the total concentration of the polyurethane and the polydiorganosiloxane is at least 4% by weight based on the weight of the emulsion composition, and the concentration of the polydiorganosiloxane is 0.1 to 50% by weight based on the total weight of it and the polyurethane.

21. The process of claim 19 wherein the polydiorganosiloxane is composed of units of the general formula

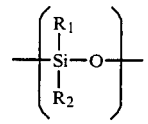

wherein $R_1$ and $R_2$ each represent an alkyl group, an aryl group, an alkenyl group or a halogenated hydrocarbon group.

22. The process of claim 19 wherein the polyurethane is obtained by chain-extending a prepolymer having isocyanate groups at the terminals of the molecular chain with a hydroxyl group-containing compound.

23. The process of claim 19 or 21 wherein the polydiorganosiloxane has at the ends of the molecular chain an active group selected from a hydroxyl group, an acetate group and a vinyl group.

24. The process of claim 19 wherein the cyclic ether is selected from tetrahydrofuran and dioxane.

25. The process of claim 21 wherein the total concentration of the polyurethane and the polydiorganosiloxane is at least 4% by weight, based on the weight of the emulsion composition, and the concentration of the polydiorganosiloxane is 0.1 to 50% by weight, based upon the total weight of it and the polyurethane.

26. The process of claim 19 wherein the crosslinking agent is used in an amount of 2 to 20% by weight, based on the polydiorganosiloxane.

27. The process of claim 19 wherein the crosslinking agent is used in an amount of 4 to 15% by weight, based on the polydiorganosiloxane.

28. The process of claim 19 wherein the crosslinking agent is used in an amount of 6 to 10% by weight, based on the polydiorganosiloxane.

29. The process of claim 26 wherein the crosslinking agent is a compound of the general formula $$R_nSi(OR')_{4-n}$$

wherein R represents an alkyl group or an aryl group, R' represents an alkyl group or an acyl group, and n is 0 to 1.

30. The process of claim 19 wherein the cyclic ether is a mixture of dioxane to tetrahydrofuran at a ratio of from 1:1 to 1:4.

31. The process of claim 19 wherein the total concentration of the polyurethane and the polydiorganosiloxane is from 8 to 20% by weight, based on the emulsion composition and the concentration of the polydiorganosiloxane is 0.5 to 30% by weight, based on the total weight of it and the polyurethane.

32. The process of claim 19 wherein the reaction between the polydiorganosiloxane with the crosslinking agent is carried out in the presence of from 50 to 300 ppm of water.

33. The process of claim 19 wherein the reaction between the polydiorganosiloxane with the crosslinking agent is carried out in the presence of from 80 to 200 ppm of water.

* * * * *

UNITED STATES PATENT AND TRADEMARK OFFICE
CERTIFICATE OF CORRECTION

PATENT NO. : 4,604,412

DATED : August 5, 1986

INVENTOR(S) : Yasushi Joh, et al.

It is certified that error appears in the above-identified patent and that said Letters Patent is hereby corrected as shown below:

IN THE CLAIMS

Claim 2, lines 3-4, (column 10, lines 45-46),
delete "polyorganosiloxane",
insert --polydiorganosiloxane--.

Signed and Sealed this

Twenty-eighth Day of October, 1986

[SEAL]

*Attest:*

DONALD J. QUIGG

*Attesting Officer*   *Commissioner of Patents and Trademarks*